United States Patent
Koehler et al.

(10) Patent No.: US 10,368,815 B2
(45) Date of Patent: Aug. 6, 2019

(54) X-RAY IMAGING DEVICE

(71) Applicant: KONINKLIJKE PHILIPS N.V., Eindhoven (NL)

(72) Inventors: Thomas Koehler, Norderstedt (DE); Ewald Roessl, Ellerau (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 76 days.

(21) Appl. No.: 15/325,551

(22) PCT Filed: Jul. 7, 2015

(86) PCT No.: PCT/EP2015/065405
§ 371 (c)(1),
(2) Date: Jan. 11, 2017

(87) PCT Pub. No.: WO2016/088762
PCT Pub. Date: Jan. 21, 2016

(65) Prior Publication Data
US 2017/0156686 A1    Jun. 8, 2017

(30) Foreign Application Priority Data

Jul. 17, 2014    (EP) ..................................... 14177486

(51) Int. Cl.
*A61B 6/00*    (2006.01)
*A61B 6/06*    (2006.01)
(Continued)

(52) U.S. Cl.
CPC .............. *A61B 6/4035* (2013.01); *A61B 6/06* (2013.01); *A61B 6/4291* (2013.01);
(Continued)

(58) Field of Classification Search
CPC .................................................... A61B 6/484
See application file for complete search history.

(56) References Cited

U.S. PATENT DOCUMENTS

| 5,400,379 A | 3/1995 | Pfoh |
| 9,031,189 B2 | 5/2015 | Mukaide |

(Continued)

FOREIGN PATENT DOCUMENTS

| JP | 2014100063 A | 5/2014 |
| WO | 2012/029005 | 3/2012 |

(Continued)

OTHER PUBLICATIONS

Donath et al, "Inverse geometry for grating based x-ray phase contrast imaging", Journal of Applied Physics 106, 054703, 2009.
(Continued)

*Primary Examiner* — Dani Fox
(74) *Attorney, Agent, or Firm* — Larry Liberchuk (57) ABSTRACT

The invention relates to X-ray imaging. In order to improve flexibility, for example in relation with phase-contrast imaging, the X-ray imaging device (10) comprises an X-ray source arrangement for providing an X-ray beam (11). Further, it is provided at least one grating (13, 14) and a line detector (15) with a plurality of sensor lines, which sensor lines are each provided by a plurality of sensor elements, and which sensor lines are provided for detecting respective portions of the X-ray beam (11) passing the at least one grating during operation. The X-ray imaging device is arranged for moving the line detector (15) and an object (21) to be imaged relative to each other, such that in response to the portions of the X-ray beam a number of interference patterns are detectable at respective different relative positions of the line detector and the object for reconstructing an image of the object (21). The at least one grating (13, 14) comprises at least one first segment (161) and at least one second segment (162) arranged adjacent to each other in a direction perpendicular to the direction of the line detector (15). The X-ray imaging device is arranged for moving the
(Continued)

line detector (15) and the at least one grating relative to each other between at least a first relative position and a second relative position, such that in the first relative position, a portion of the X-ray beam (11) during operation passes through the at least one first segment (161), while the at least one second segment (162) is arranged outside said portion of the X-ray beam (11), and that in the second relative position, said portion of the X-ray beam (11) during operation passes through the at least one second segment (162), while the at least one first segment (161) is arranged outside said portion of the X-ray beam (11).

14 Claims, 3 Drawing Sheets (51) Int. Cl.
  *G01N 23/083* (2018.01)
  *A61B 6/04* (2006.01)
(52) U.S. Cl.
  CPC ............ *A61B 6/4435* (2013.01); *A61B 6/484* (2013.01); *A61B 6/54* (2013.01); *G01N 23/083* (2013.01); *A61B 6/0414* (2013.01); *A61B 6/4208* (2013.01); *A61B 6/4429* (2013.01); *A61B 6/502* (2013.01)

(56) References Cited

U.S. PATENT DOCUMENTS

| | | |
|---|---|---|
| 2010/0177864 A1 | 7/2010 | Donath |
| 2010/0272235 A1 | 10/2010 | Takahashi |
| 2012/0039446 A1 | 2/2012 | Cui |
| 2012/0189101 A1 | 7/2012 | Kaneko |
| 2013/0202081 A1* | 8/2013 | Rossl .................... A61B 6/484 378/36 |
| 2014/0177795 A1 | 6/2014 | Spahn |
| 2014/0286475 A1 | 9/2014 | Nakamura |
| 2015/0036795 A1 | 2/2015 | Roessl |

FOREIGN PATENT DOCUMENTS

| | | |
|---|---|---|
| WO | 2012052900 | 4/2012 |
| WO | 2013/111050 | 8/2013 |
| WO | 2015/044001 | 4/2015 |

OTHER PUBLICATIONS

Sato, et al., "Single-Shot X-Ray Phase-Contrast Imaging Using Two-Dimensional Gratings", International Workshop on X-ray and Neutron Phase Imaging with Gratings, AIP Conf. Proc. 1466, 29-34 (2012).

* cited by examiner

X-RAY IMAGING DEVICE

CROSS REFERENCE TO RELATED APPLICATIONS

This application is the U.S. National Phase application under 35 U.S.C. § 371 of International Application No. PCT/EP2015/065405, filed Jul. 7, 2015, published as WO2016/008732 on Jan. 21, 2016, which claims the benefit of European Patent Application Number 14177486.9 filed Jul. 17, 2014. These applications are hereby incorporated by reference herein.

FIELD OF THE INVENTION

The invention relates to an X-ray imaging device, an X-ray imaging system, an X-ray imaging method, a computer program element for controlling such device and a computer readable medium having stored such computer program element.

BACKGROUND OF THE INVENTION

When acquiring an X-ray image, an object to be examined, e.g. a patient, is arranged between an X-ray generating device and an X-ray detector. X-ray radiation emanating from the X-ray generating device is penetrating the object to be examined, subsequently arriving at the X-ray detector. The object to be examined, situated in the path of the X-ray radiation is spatially attenuating the X-ray beam, depending on the specific tissue structure within the object. The X-ray detector is subsequently detecting the spatially attenuated X-ray radiation by determining an intensity distribution of the X-ray radiation, which image information is employed for generating, further processing, and subsequently displaying an X-ray image of the object to be examined.

However, an object to be examined may provide only minor differences when attenuating the X-ray radiation, resulting in a relatively uniformly attenuated X-ray image having low contrast, thus lacking detail of the imaged inner structure of the object.

While certain objects or regions within an object may comprise similar attenuation properties, a phase of X-ray radiation penetrating the object may be influenced to a larger extent by the structure of the object.

In phase-contrast imaging, at least partly coherent X-ray radiation is employed, e.g., generated by a source grating arranged adjacent to, in the vicinity of an X-ray source, e.g. an X-ray tube. Coherent X-rays penetrating the object may allow for subsequent retrieval of phase information.

However, a phase of a wave may not be measured directly, rather a phase-shift may be required to be converted to an intensity modulation, e.g., by interfering two or more waves. For generating an according interference pattern, a so-called phase grating is employed, arranged between the object to be examined and an X-ray detector. However, an interference pattern generated by only employing a phase grating may be too small to be detectable with a current X-ray detector, due to a lack of spatial resolution of the X-ray detector.

Thus, a further analyzer grating may be employed arranged between the phase grating and the X-ray detector, subsequently providing an interference pattern, which is large enough to be detectable by current X-ray detectors.

To obtain appropriate image information, a so-called phase stepping is performed. In phase stepping, one of the source grating, the phase grating, and the analyzer grating is displaced laterally with respect to the other grating and the X-ray detector element by a fraction of its grating pitch, e.g., a fourth, sixth, eighth of the grating pitch, e.g. of the phase grating. If the phase stepping is performed using a particular grating, then the phase stepping shall cover a full period of this particular grating.

An alternative to the phase stepping is the so-called slit scanning approach. The object, e.g. a woman's breast, is scanned by a scan arm or gantry movement. The redundancy of the data acquisition by means of an arrangement of a number of parallel detector lines can be exploited to eliminate the need for phase-stepping and the gratings need not be moved with respect to each other. Hence, the phase-acquisition can be implemented in the ordinary scanning motion.

Employing such phase grating, in addition the generation of image data deriving from de-coherent X-ray small angle scattering is enabled, the latter type of imaging also being referred to as "dark-field imaging".

WO 2012/029005 A1 discloses an apparatus for phase-contrast imaging comprising an X-ray source, a first grating element, a second grating element and an X-ray detector element comprising a plurality of detector pixel elements. An object to be imagined is arrangeable between the X-ray source and the X-ray detector element. The first grating element as well as the second grating element is arrangeable between the X-ray source and the X-ray detector element. The X-ray source, the first grating element, the second grating element and the X-ray detector are operatively coupled for acquisition of a phase-contrast image of the object.

However, such imaging devices can be still improved, in particular in view of the flexibility and adaptability to different patients and operation conditions.

SUMMARY OF THE INVENTION

Hence, there may be a need to provide an X-ray imaging device, which is improved in view of its flexibility.

The problem of the present invention is solved by the subject-matters of the independent claims, wherein further embodiments are incorporated in the dependent claims. It should be noted that the aspects of the invention described in the following apply also to the X-ray imaging device, the X-ray imaging system, the X-ray imaging method, the computer program element, and the computer readable medium.

According to the present invention, an X-ray imaging device is presented. The X-ray imaging device comprises an X-ray source arrangement for providing an X-ray beam, at least one grating, and a line detector with a plurality of sensor lines, which sensor lines are each provided by a plurality of sensor elements, and which sensor lines are provided for detecting respective portions of the X-ray beam passing the at least one grating during operation. The line detector may comprise several one dimensional sensors forming the several sensor lines.

The X-ray imaging device is arranged for moving the line detector and an object to be imaged relative to each other, such that in response to the portions of the X-ray beam a number of interference patterns are detectable at respective different relative positions of the line detector and the object for reconstructing an image of the object. This means, the X-ray imaging device, the line detector and/or the object can be moved.

The at least one grating comprises at least one first segment and at least one second segment arranged adjacent to each other in a direction perpendicular to the direction of the line detector, and to the X-ray beam direction. The at least one grating may be placed in front of each sensor line, when seen in the X-ray beam direction. In case the X-ray imaging device is an X-ray differential phase contrast imaging device, the at least one grating may be a phase grating and/or an absorber grating.

The X-ray imaging device is arranged for moving the line detector and the at least one grating relative to each other between at least a first relative position and a second relative position, such that in the first relative position, a portion of the X-ray beam during operation passes through the at least one first segment, while the at least one second segment is arranged outside said portion of the X-ray beam, and that in the second relative position, said portion of the X-ray beam during operation passes through the at least one second segment, while the at least one first segment is arranged outside said portion of the X-ray beam.

The X-ray imaging device according to the present invention consequently enables activating the at least first segment while de-activating the at least second segment, and vice versa, thereby increasing clinical flexibility.

The X-ray imaging device may realize the movement from the first relative position to the second relative position via moving, e.g. translating in a direction perpendicular to the direction of the line detector, the at least one grating with respect to the line detector.

Each segment of the at least one grating, i.e. each of the first and the second segments, may comprise a grating structure of a respective transmission characteristic. For example, the grating structure comprises lines arranged as a sort of linear stripes of a respective transmission characteristic, also referred to as transmission function of the grating structure. The first and the second segments differ in terms of the respective grating structure such that the first and the second segments differ in terms of the respective transmission characteristic. With the term "different transmission characteristic" or "different transmission function" different absorption properties and/or different properties in view of a phase shift are meant. The grating structures may form a plurality of bars and gaps arranged periodically. The bars may be arranged to change a phase and/or amplitude of an X-ray radiation. The gaps may change a phase and/or amplitude of an X-ray radiation to another, in particular lesser degree than the bars. The gaps may be X-ray transparent. The term "X-ray transparent" means that X-ray radiation passing is not changed in its phase, i.e. it is not phase shifted, and not changed in its amplitude, both to a measureable or reasonable amount.

In an example, the X-ray imaging device comprises a displacement unit configured for moving the at least one at least one grating relative to the line detector.

In an example, the X-ray imaging device is arranged for moving the line detector and the at least one grating relative to each other between at least a first relative position and a second relative position. In the first relative position, the at least one first segment projects along the X-ray beam onto the sensor line such that the portion of the X-ray beam that during operation passes through the at least one first segment subsequently arrives at the one-dimensional sensor line for detection, while the at least one second segment is arranged outside the portion of the X-ray beam such that it projects along the X-ray beam onto the area between neighboring sensor lines. In the second relative position, the at least one second segment projects along the X-ray beam onto the sensor line such that the portion of the X-ray beam that during operation passes through the at least one second segment subsequently arrives at the one-dimensional sensor line for detection, while the at least one first segment is arranged outside the portion of the X-ray beam such that it projects along the X-ray beam onto the area between neighboring sensor lines. The X-ray imaging device according to this example effectively utilizes the distance (in a direction perpendicular to the direction of the line detector) between neighboring sensor lines to "hide" the at least one second segment in the first relative position, and to "hide" the at least one first segment in the second relative position. Typically, the distance between neighboring sensor lines is a multiple of the height of a sensor line. The movement from the first relative position to the second relative position may be realized by moving, e.g. translating in a direction perpendicular to the direction of the line detector, the at least one grating with respect to the line detector.

In an example, the X-ray imaging comprises a pre-collimator to divide the X-ray beam into respective portions, and more specifically to generate a sliced X-ray beam. Herein, the pre-collimator is arranged for slicing the X-ray beam such that the slices of the X-ray beam during operation will illuminate or project onto respective sensor lines. In an example, the at least one grating comprises a frame and the frame comprises at least the first and second segments.

The relative position of the first and second segments as supported by the frame is preferably accurate and stable within sub-micrometer accuracy. Therefore, the frame may be realized in a mechanically very stiff manner e.g. using steel or Invar.

As a result, an X-ray imaging device is provided, which is improved in view of its flexibility, since it enables easy and fast switching between different segments of the grating. Thereby, the X-ray imaging device can be easily and fast adapted to different operation conditions, patients and e.g. breast volumes by simply switching to the segment, which is in particular suitable for the current situation.

It is noted that at least one grating is provided. For example, two or three gratings are provided. Nevertheless, in the following, and also in the claims, the "at least one grating" is also referred to as "grating", i.e. without the term "at least one" in order to provide better readability. However, the "grating" also relates to at least one grating, where applicable.

The line detector employed in the present invention has a pitch sufficiently small, hence a resolution sufficiently large, for detecting i.e. adequately resolving the interference pattern generated by the phase grating. For that purpose such line detector may be a high resolution X-ray detector known per se having a resolution of 50 micrometers or more, or an X-ray detector equivalent to the type as described in US 2014/0177795 A1 which is incorporated herein by reference. Alternatively, the line detector may have high resolution when used in conjunction with an analyzer grating i.e. an absorption grating arranged in the optical path between the phase grating and said line detector.

It is also noted that the at least one grating is provided with at least one first segment and at least one second segment. For example, two, three, four, five or more first and/or second segments are provided. Nevertheless, in the following, and also in the claims, the "at least one first (or second) segment" is also referred to as "first (or second) segment", i.e. without the term "at least one" in order to provide better readability. However, the "first (or second) segment" also relates to at least one first (or second) segment, where applicable.

In an example, the X-ray imaging device is an X-ray differential phase contrast imaging device. Differential phase contrast imaging may employ a set of gratings installed between the X-ray source and the X-ray detector in order to retrieve phase information. The X-ray source arrangement may be an X-ray source with or without a source grating. The grating may be a phase grating or an absorber grating. The grating may be placed in front of each sensor line of the line detector, when seen in the X-ray beam direction. The first and the second segments may differ from each other in view of the grating lines. Options for differencing the grating lines are e.g. a differing pitch and/or a differing orientation, as shown in the following.

It is noted that the terms "absorber grating" and "phase grating" relate to the function of the grating in terms of their effect on the passing X-ray radiation. However, the terms in a certain sense may also relate to the location or position within an interferometer used for phase contrast imaging. For example, a grating as a phase grating may be provided as a first grating, also known as G1 with pitch $p_1$, where G0 with pitch $p_0$ refers to a source grating, and another optionally (depending on the implementation of the line detector) grating may be provided as analyzer grating, or G2 with pitch $p_2$, in front of the line detector. Introducing s as the distance between G0 and G2, l as the distance between G0 and G1 and d as the distance between G1 and G2 (if any), the various geometries can be defined on the basis of said quantities. As a first option, the interferometer may be implemented in the so-called "conventional geometry" in which l>d and $p_0$>$p_1$>1$p_2$. In the conventional geometry, the object to be imaged is typically arranged between G0 and G1. As a second option, the interferometer may be implemented in the so-called "inverse geometry" in which l<d and $p_0$<$p_1$<$p_2$. In the inverse geometry, the object to be imaged is typically arranged between G1 the X-ray detection unit (i.e. between G1 and G2 in case G2 is present). As a third option, the interferometer may be implemented in the so-called "symmetric geometry" in which d=l and $p_0$=p1=$p_2$ (presuming a π-shifting grating G1). For more information (incorporated herein by reference) see Tilman Donath et al, "Inverse geometry for grating based x-ray phase contrast imaging", JOURNAL OF APPLIED PHYSICS 106, 054703, 2009.

In an example, the grating is a source grating. The source grating may be provided as absorber grating, in terms of the function of the grating. The source grating may also be provided as phase grating, in terms of the function of the grating.

A design energy of a grating interferometer is the energy, where the device performs (at least theoretically) best. Considering for example a Talbot interferometer with a phase grating 7C and a design energy $E_d$, a height of trenches of the phase grating need to be selected such that the desired phase change of the phase grating π is achieved. For a given and constant distance d between the phase grating and the absorber grating, the pitch of the phase grating must fulfill the relation $p^2$=8 n d $\lambda_d$ with n being an odd integer and $\lambda_d$ being the wavelength of photons at the design energy. The pitch of the source grating needs then to be adjusted to the pitch of the phase grating. As a result, it is not easy to change the design energy of a Talbot-Lau interferometer. For a good practical performance, the voltage of the X-ray tube needs to be tuned such that the peak of the spectrum transmitted through the object is close to the design energy. Therefore, in an example, the grating structure of the first segment has a first grating pitch, and the grating structure of the second segment has a second grating pitch that differs from the first grating pitch. As "pitch", the distance between two adjacent grating lines is to be understood. The first segment may have a relatively large grating pitch, hence being suitable for relatively low design energy.

The second segment may have a relatively small grating pitch, hence being suitable for relatively high design energy.

As a result, the design energy can be changed easily. Further, an interferometer design for differential phase contrast imaging is provided that allows picking for each scan a proper design energy for a current patient. For a given patient, e.g. a breast thickness is known before the scan and a suitable grating with appropriate design energy can be moved in front of each line detector sensor before the scan.

As the grating may comprise a grating structure, such as grating lines, which are also referred to as line structures, the interferometer may have an anisotropic sensitivity. This means, e.g. if the grating lines are parallel to the detector lines, only object structures parallel to the lines are detectable. Object structures oriented perpendicular to the lines can be barely detectable. Therefore, a detection of phase gradients in mutually perpendicular directions is desirable, which can be achieved as shown in the following. In an example, the grating structure, for example grating lines, of the first segment has a first orientation, and the grating structure, for example also grating lines, of the second segment has a second orientation that differs from the first orientation. In other words, the grating to be installed on the detector comprises a first segment with a grating structure in some direction "x", and a second segment with a grating structure in some direction "y", which is pivoted relative to x. In an example, the first and second orientations are essentially perpendicular to each other.

As a result, a very accurate detection of phase gradients in mutually perpendicular directions is achieved. Further, an interferometer design for differential phase contrast imaging is provided that facilitates the acquisition of both gradient directions with two subsequent scans. With these structures in place, it is simple to acquire e.g. two gradients by (i) scanning in one direction employing the first relative position, (ii) relatively moving the line detector and the grating relative from the first to the second relative position after scanning in said one direction, and (iii) subsequently scanning in reversed direction employing the second relative position. The X-ray imaging device is preferably configured for rotating the source grating by 90° around the optical axis between these two scans in case the source grating is provided with a single segment rather than first and second segments that are respectively compatible with the first and second segments of the at least one grating.

In an example, the grating structure of the first segment and the grating structure of the second segment, and possibly also the grating structure of the third or more segment, differs from the respective other grating structures of the other segments in terms pitch and/or geometry and/or orientation.

In an example, the grating with the first segment and the second segment may comprise similar or different grating structures in the first segment and the second segment. It is e.g. possible to have a combination of a phase grating structure, e.g. phase grating lines, in the first segment and an absorber grating structure, e.g. absorber grating lines, in the second segment of the grating, e.g. as the same frame of the same grating.

Of course, there may be even more segments with more discrete design energies and/or more discrete orientations. In an example, the grating comprises at least one third segment arranged adjacent to the second segment in a direction perpendicular to the direction of the line detector, wherein the at least one third segment differs from the first and the second segments in terms of the respective grating structure and the respective transmission characteristic. The X-ray imaging device is arranged for moving the line detector and the at least one grating relative to each also to a third relative position, such that in the third relative position, the portion of the X-ray beam during operation passes through the at least one third segment, while the first and second segments are arranged outside said portion of the X-ray beam, and that in the first and second relative position, the at least one third segment is arranged outside said portion of the X-ray beam.

In an example, the three segments differ in view of their grating pitches. In another example, one segment A is provided for the acquisition of conventional data, one segment B is provided for the acquisition of gradients in a direction "x", and one segment C is provided for the acquisition of gradients in direction "y", wherein y is pivoted relative to x. This structure facilitates three different operation modes: if the segment A is installed such that it projects onto a sensor line, conventional scanning is performed, if segment B is installed such that it projects onto the sensor line a gradient in x-direction is measured, and if segment C is installed such that it projects onto the sensor line, a gradient in y-direction is measured, wherein x differs from y.

The anisotropy in phase-sensitivity can be further reduced by employing at least a further segment with a grating orientation of e.g. 45° in between the first and second segments perpendicular to each other.

In an example, the grating structure of the first segment has a first geometry, and the grating structure of the second segment has a second geometry that differs from the first geometry.

In an example, the grating is provided with different grating geometries for the first and second, or also the third, segments. For example, the grating geometries are provided as linear structure, or as triangular structure, or as rectangular structure, or as parabolic structure and the like. Due to the movability of the grating in respect to the X-ray beam, it is possible to switch between various grating geometries.

In an example, the grating is a source grating arranged adjacent to the X-ray source and generating at least partly coherent X-ray radiation. The source grating may then comprise a frame, a first segment and a second segment arranged adjacent to each other in a direction perpendicular to the direction of the line detector. The frame may be movable between a first relative position and a second relative position, such that in the first position, the X-ray beam passes through the first segment, while the second segment is arranged outside the X-ray beam, and in the second position, the X-ray beam passes through the second segment, while the first segment is arranged outside the X-ray beam. The first and second segments of the source grating need not be identical to those of the a least one grating, however, they should be respectively compatible with the first and second segments of the at least one grating such as to constitute a functional interferometric unit.

In an example, the X-ray imaging device is an X-ray differential phase contrast imaging device and the at least one grating is provided as a phase grating, or as an absorber grating.

In an example, two gratings of the at least one grating are provided. One of the two gratings is a phase grating and the other one of the two gratings is an absorber grating installed relative to the phase grating downstream the X-ray beam.

In an example, the first segments of the phase grating are different than the first segments of the absorber grating, and/or the second segments of the phase grating are different than the second segments of the absorber grating. In another example, the first segments of the phase grating are equal to the first segments of the absorber grating, and/or the second segments of the phase grating are equal than the second segments of the absorber grating.

In another example, the grating is a phase grating followed, along the direction of the X-ray beam, by an absorber grating, whereby the phase grating and the absorber grating each comprise the grating structure as explained above. The absorber grating may be adapted to the phase grating, which means that pitch and/or orientation of the absorber grating is selected corresponding to pitch and/or orientation of the interference pattern generated by the phase grating at the position of the absorber grating. With these structures in place, it is relatively simple to acquire e.g. two gradients by scanning in one direction with the first segment and immediately after the scan with reversed scan direction with the second segment. The X-ray imaging device, in case the source grating is provided with a single segment rather than first and second segments that are respectively compatible with the first and second segments of the at least one grating such as to constitute a functional interferometric unit, is preferably configured for rotating the source grating by 90° around the optical axis between these two scans.

In an example, the phase grating can be provided with a triangular shape, which leads to higher visibilities for shorter propagation distances compared to gratings with binary structures.

In an example, the X-ray imaging device is not (only) an X-ray differential phase contrast imaging device evaluating differential phase contrast, but additionally or instead a device for evaluating a dark field also supplied by an Talbot interferometer. In an example, the detector lines are about 110 μm high. The grating may be a grating pair mounted to a frame. The frame may be a rigid steel frame.

In an example, the grating and the line detector are mounted to a movable gantry to be movable with respect to the object, such that in response to the X-ray beam a number of interference patterns from different positions of the gantry are detectable for reconstructing a differential phase image of the object. In another example, the X-ray source, the source grating, the phase grating, the absorber grating and the line detector are fixed to a common gantry and are movable with respect to the object, such that in response to the X-ray beam a number of interference patterns from different positions of the gantry are detectable for reconstructing a differential phase image of the object. Further, the X-ray imaging device may comprise a gantry displacement unit configured to move the gantry with respect to the object to be imaged.

In an example, a gantry displacement unit is provided that is configured for moving the movable gantry relative to the object to be imaged.

According to the present invention, also a medical X-ray imaging system is presented. The X-ray imaging system comprises an X-ray imaging device as described above, a processing unit, and an object-receiving device configured to receive an object to be imaged. The processing unit is configured to control a relative movement of the X-ray imaging device and the object-receiving device in relation to each other. Additionally or instead, the processing unit is configured to control a relative movement of the at least one grating and the line detector of the X-ray imaging device in relation to each other.

The X-ray imaging system may be used for a scanning phase contrast mammography system with a selectable design energy. The X-ray imaging system may also be used for a scanning system that acquires gradients in both directions.

According to the present invention, also an X-ray imaging method is presented. It comprises the following steps, not necessarily in this order:

providing an X-ray beam with an X-ray source arrangement to an object to be imaged;

generating an interference pattern with at least one grating that comprises at least a first segment and a second segment arranged adjacent to each other in a direction perpendicular to the direction of a line detector;

relatively moving a line detector with a plurality of sensor lines, which sensor lines are each provided by a plurality of sensor elements, and which sensor lines are provided for detecting respective portions of the X-ray beam passing the grating during operation and the object to be imaged, such that in response to the portions of the X-ray beam a number of interference patterns are detected at respective different relative positions of the line detector and the object for reconstructing an image of the object;

relatively moving the line detector and the grating between at least a first relative position and a second relative position, such that in the first relative position, a portion of the X-ray beam during operation is passing through the at least one first segment, while the at least one second segment is arranged outside the portions of the X-ray beam, and that in the second relative position, said portion of the X-ray beam during operation is passing through the at least one second segment, while the at least one first segment is arranged outside said portion of the X-ray beam; and detecting the portion of the X-ray beam passing the grating.

According to the present invention, also a computer program element is presented, wherein the computer program element comprises program code means for causing an imaging device as defined in the independent device claim to carry out the steps of the imaging method as defined in the independent method claim, when the computer program is run on a computer controlling the imaging device.

It shall be understood that the X-ray imaging device, the X-ray imaging system, the X-ray imaging method, the computer program element for controlling such device and the computer readable medium having stored such computer program element according to the independent claims have similar and/or identical preferred embodiments, in particular, as defined in the dependent claims. It shall be understood further that a preferred embodiment of the invention can also be any combination of the dependent claims with the respective independent claim.

The X-ray imaging device, the X-ray imaging system, the X-ray imaging method, the computer program element for controlling such device and the computer readable medium having stored such computer program element according to the present invention are configured for phase contrast imaging and/or dark-field imaging. The present invention allows for useful application in a clinical environment such as a hospital. More specifically, the present invention is very suitable for application in imaging modalities, including without limitaiton, for the medical examination of patients. In addition, the presentation invention allows for useful application in an industrial environment. More specifically, the present invention is very suitable for application in non-destructive testing (e.g. analysis as to composition, structure and/or qualities of biological as well non-biological samples) as well as security scanning (e.g. scanning of luggage on airports).

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings.

DETAILED DESCRIPTION OF EMBODIMENTS

Figure 1:
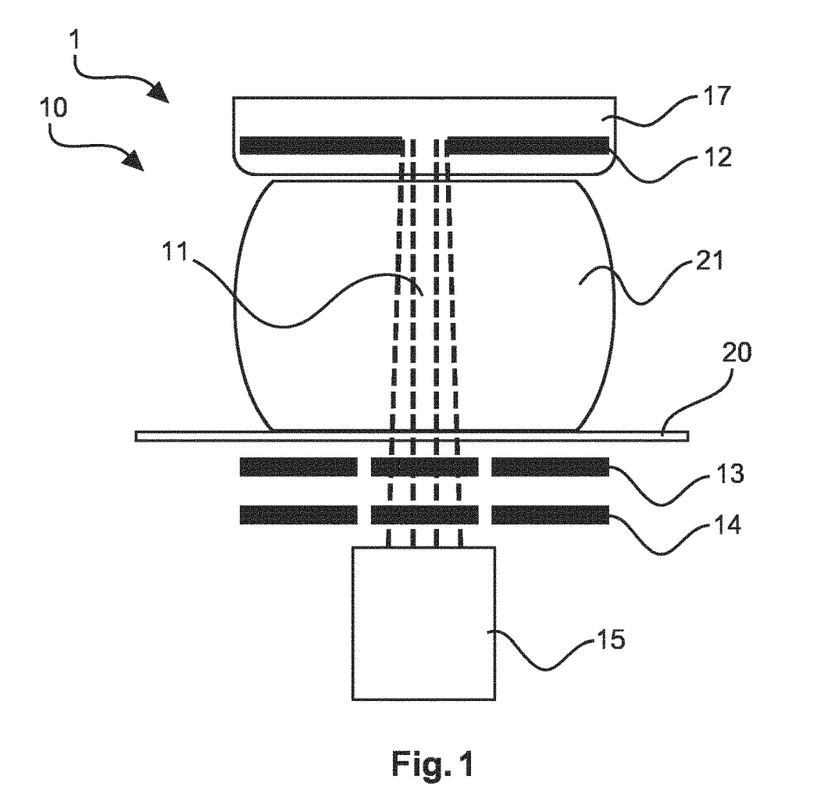
FIG. 1 shows a schematic drawing of an example of an X-ray imaging system.

FIG. 1 shows schematically and exemplarily an embodiment of an X-ray imaging system 1 according to the invention. Note that the vertical and the horizontal axes are scaled differently. The X-ray imaging system 1 is suitable for phase-contrast imaging and comprises an X-ray imaging device 10, a processing unit (not shown) and an object-receiving device 20. The object-receiving device 20 is configured to receive an object 21 to be imaged, which is here shown as a breast compressed by a compression plate 17. The X-ray imaging device 10 comprises an X-ray source (not shown) providing an X-ray beam 11, a source grating 12, a phase grating 13, an absorber grating 14, and a line detector 15 comprising a plurality of sensor lines 151, which sensor lines 151 are each provided by a plurality of sensor elements, and which sensor lines are provided for detecting respective portions of the X-ray beam 11 passing the gratings 12, 13, 14 during operation.

At least partly spatially coherent X-ray radiation is generated by the source grating 12 arranged adjacent to the X-ray source, which is here an X-ray tube. Coherent X-rays then penetrating the object 21 may allow for subsequent retrieval of phase information. As a phase of a wave may not be measured directly, rather a phase-shift is required to be converted to an intensity modulation by interfering two or more waves. For generating a corresponding interference pattern, the phase grating 13 is employed, which is arranged between the object 21 to be examined and the X-ray detector 15. As the interference pattern generated by the phase grating 13 may be too small to be detectable with the X-ray detector 15, due to a lack of spatial resolution of the X-ray detector 15, the absorber or analyzer grating 14 is arranged between the phase grating 13 and the X-ray detector 15 for subsequently providing an interference pattern, which is large enough to be detectable by the X-ray line detector 15.

Figure 2:
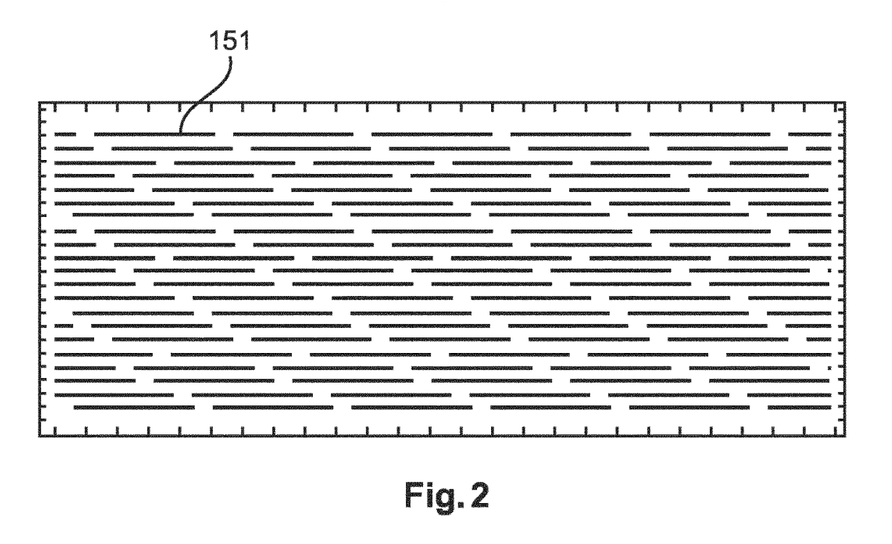
FIG. 2 shows schematically and exemplarily a detector geometry.

The line detector 15 comprises several (more or less) one-dimensional sensors provided by a plurality of sensor elements, the sensor elements forming several sensor lines 151. FIG. 2 shows schematically and exemplarily a detector geometry. Each sensor line 151 in FIG. 2 represents a sensor with e.g. up to 768 detector pixels.

The X-ray imaging device 1 is arranged for moving the line detector 15 and an object 21 to be imaged relative to each other, such that in response to the portions of the X-ray beam a number of interference patterns are detectable at respective different relative positions of the line detector 15 and the object 21 for reconstructing an image of the object 21.

In view of the linear extension (i.e. direction) of the sensor lines of the detector, a direction parallel to the linear extensions of the line detector is referred to as a direction of the line detector. In FIG. 2 the direction of the line detector runs parallel to the sensor lines 151, i.e. horizontally with respect to the drawing page.

Figure 3:
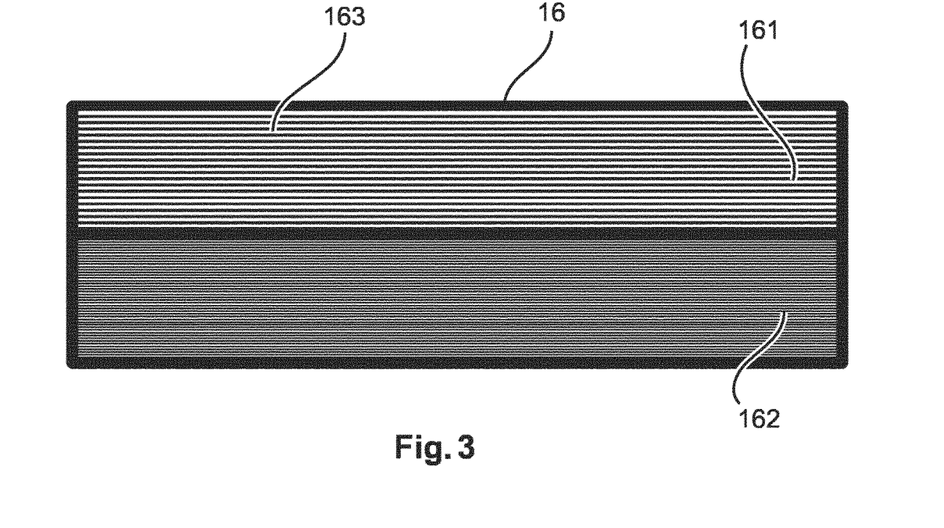
FIG. 3 shows schematically and exemplarily an embodiment of a grating
Figure 4:
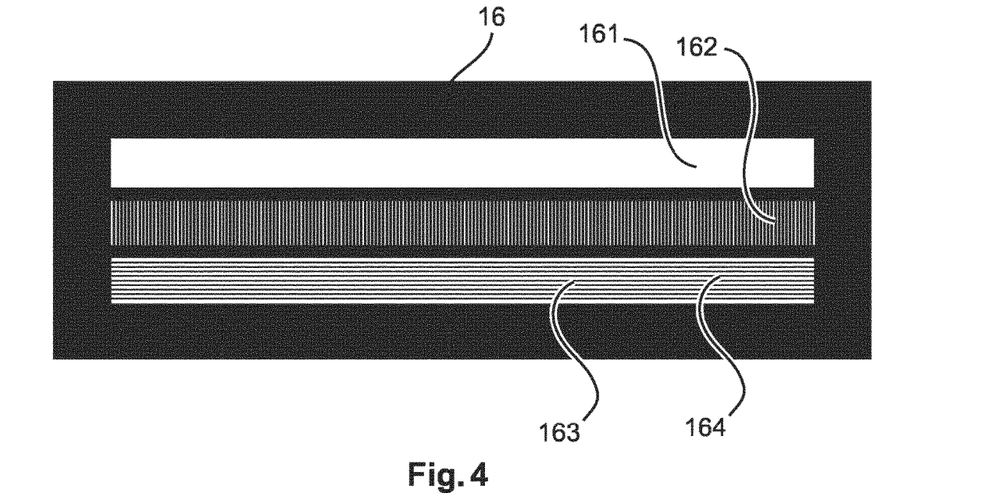
FIG. 4 shows schematically and exemplarily another embodiment of a grating.
Figure 5:
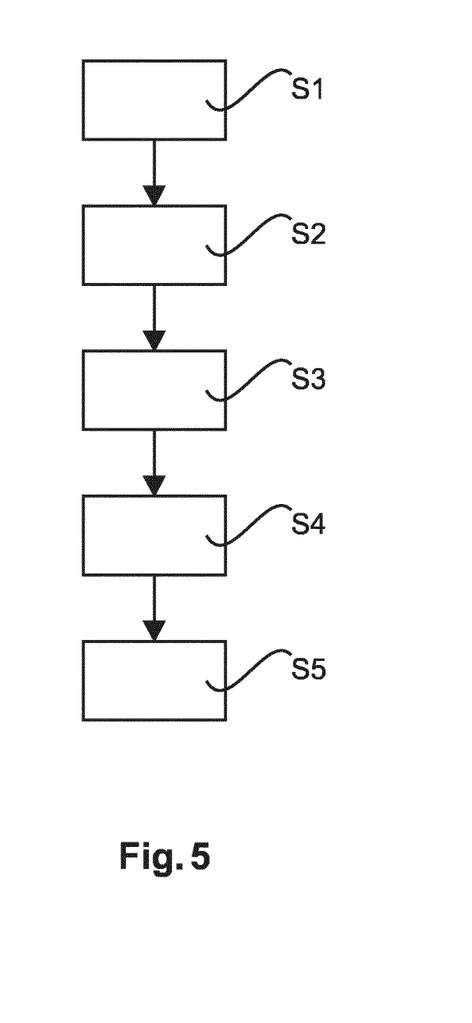
FIG. 5 shows basic steps of an example of an X-ray imaging method.

FIGS. 3 and 4 schematically and exemplarily show embodiments of a grating. As can be seen in FIGS. 3 and 4, at least one of the source grating 12, the phase grating 13 or the absorber grating 14 comprises at least one first segment 161 and at least one second segment 162 arranged adjacent to each other in a direction perpendicular to the direction of the line detector 15 and to the X-ray beam 11 direction. Each of the at least one first and second segments 161, 162 of the grating comprises a grating structure of a respective transmission characteristic, for example in form of grating lines 163, also referred to as stripes, of different transmission characteristic. The first and the second segments 161, 162 mutually differ in terms of the respective grating structure such that the first and the second segments 161, 162 differ in terms of the respective transmission characteristic, as will be shown further below to FIGS. 3 and 4.

Referring to FIG. 1, the X-ray imaging device 1 is arranged for moving the line detector 15 and at least one of the source grating 12, the phase grating 13 or the absorber grating 14, between a first relative position and a second relative position, such that in the first relative position, a portion of the X-ray beam during operation passes through the first segment 161 and subsequently illuminates a respective sensor line 151, while the second segment 162 is arranged outside said portion of the X-ray beam, and that in the second relative position, said portion of the X-ray beam during operation passes through the second segment 162 and subsequently illuminates said respective sensor line 151, while the first segment 161 is arranged outside said portion of the X-ray beam. X-ray imaging device 1 may realize the movement from the first relative position to the second relative position by moving, e.g. translating in a direction perpendicular to the direction of the line detector 15, at least one of the source grating 12, the phase grating 13 or the absorber grating 14 with respect to the line detector 14. The X-ray imaging device may employ an actuator known per se to the person skilled in the art for realizing such movement between the first and second relative positions.

Referring to FIGS. 3 and 4, in an example, at least one of the source grating 12, the phase grating 13 or the absorber grating 14 comprises a plurality of first segments 161 and an identical plurality of second segments 162. More specifically, the pluralities of segments 161, 162 equal the number of sensor lines 151 as comprised in the line detector 15. Herein the first segments 161 and the second segments 162 are arranged adjacent to each other, in alternating manner, in a direction perpendicular to the direction of the line detector 15. In this example, the X-ray imaging device 1 is arranged for moving the line detector 15 and at least one of the source grating 12, the phase grating 13 or the absorber grating 14, between a first relative position and a second relative position. In the first relative position, the portions of the X-ray beam during operation pass through respective first segments 161 and subsequently illuminate respective sensor lines 151 of the line detector 15 for detection, while the second segments 162 are arranged outside said portions of the X-ray beam. More specifically, in the second relative position the second segments 162 project along the X-ray beam onto respective spaces between neighboring sensor lines 151. In the second relative position, the portions of the X-ray beam during operation pass through respective second segments 162 and subsequently illuminate said respective sensor lines 151 of the line detector 15 for detection, while the first segments 161 are arranged outside said portions of the X-ray beam. More specifically, in the second relative position the first segments 161 project along the X-ray beam onto said spaces between neighboring sensor lines 151.

In a further example, both the phase grating 13 and the absorber grating 14 comprise a plurality of first segments 161 and an identical plurality of second segments 162. Herein the pluralities of segments 161, 162 equal the number of sensor lines 151 as comprised in the line detector 15. The first segments 161 comprised in the phase grating 13 need not be identical to those comprised in the absorber grating 14, however, they are compatible with the first segments 161 comprised in the absorber grating 14 such that they constitute a functioning interferometric unit. This applies mutatis mutandis to the second segments 162 comprised in the phase grating 13 and those comprised in the absorber grating 14. In this example, the X-ray imaging device 1 is arranged for moving the line detector 15 and the phase grating 13 and the absorber grating 14 in combination, between the first relative position and the second relative position. In the first relative position, the portions of the X-ray beam during operation pass through respective first segments 161 of both the phase grating 13 and the absorber grating 14 and subsequently illuminate respective sensor lines 151 of the line detector 15 for detection, while the second segments 162 of both the phase grating 13 and the absorber grating 14 are arranged outside said portions of the X-ray beam. More specifically, in the second relative position the second segments 162 project along the X-ray beam onto respective spaces between neighboring sensor lines 151. In the second relative position, the portions of the X-ray beam during operation pass through respective second segments 162 of both the phase grating 13 and the absorber grating 14 and subsequently illuminate said respective sensor lines 151 of the line detector 15 for detection, while the first segments 161 of both the phase grating 13 and the absorber grating 14 are arranged outside said portions of the X-ray beam. More specifically, in the second relative position the first segments 161 project along the X-ray beam onto said spaces between neighboring sensor lines 151. In an example, shown as an option, a frame 16 is provided comprising the first and second segments.

The processing unit of the X-ray imaging system 1 is arranged for controlling a relative movement between the X-ray imaging device 10 and the object-receiving device 20. For example, the X-ray imaging system 1 is configured to keep the object-receiving device 20 stationary during operation, and to realize said relative movement by moving, e.g. rotating, a movable gantry to which the line detector 15 and the at least one grating but preferably all of the source grating 12, the phase grating 13 or the absorber grating 14 are mounted, relative to the object-receiving device 20. In an example the processing unit of the X-ray imaging system 1 is alternatively, or in addition, arranged for controlling a movement from the line detector and the at least one grating relative to each other from the first to the second relative position, and vice versa.

FIG. 3 shows schematically and exemplarily an embodiment of a grating. The grating may comprise a frame 16 comprising a first segment 161 and a second segment 162 arranged adjacent to each other in a direction perpendicular to the direction of the line detector 15. Each of the first and the second segments 161, 162 of the grating comprise grating lines 163 as stripes of different transmission characteristic, or transmission functions. The first and the second segments 161, 162 differ from each other in view of the grating lines 163. As shown in FIG. 3, the grating structure, such as the grating lines 163, of the first segment 161 has a first grating pitch and the grating structure, such as the grating lines 163, of the second segment 162 has a second grating pitch that differs from the first grating pitch. The first segment 161 has a relatively large grating pitch, hence being suitable for relatively low design energy. The second segment 162 has a relatively small grating pitch, hence being suitable for relatively high design energy.

Here, the notion is to have a rigid interferometer box with a fixed distance d between the phase grating 13 and the absorber grating 14. As sketched in FIG. 3, the grating pitch p in the first segment 161 is larger than in the second segment 162, so the fixed distance d relates to a smaller design energy that is given by the relation for the design wavelength $\lambda=p^2/8d$, or in other words, at fixed distance d, the relationship $E_{design} \propto 1/p^2$ for the design energy holds. The height of the phase gratings may also be different in order to achieve the desired phase shift. Furthermore, the shape of the gratings may be different, for example the first one may be a rectangular grating and the second one may be a triangular grating.

FIG. 4 shows schematically and exemplarily an embodiment of a grating. The grating may comprise a frame 16 (as an option) comprising a first segment 161, a second segment 162 and at least one third segment 164 arranged adjacent to each other in a direction perpendicular to the direction of the line detector 15 and to the X-ray beam 11 direction. Each of the three segments of the grating comprises grating lines 163 of different transmission characteristic. In an example, the X-ray imaging device is arranged for moving the line detector 15 and the at least one grating relative to each also to a third relative position, such that in the third relative position, the portions of the X-ray beam during operation pass through the at least one third segment, while the first and second segments 161, 162 are arranged outside the portions of the X-ray beam, and that in the first and second relative position, the at least one third segment is arranged outside the portions of the X-ray beam.

In an example, a first segment 161 is provided for the acquisition of conventional data, a second segment 162 is provided for the acquisition of gradients in an orientation "x", and a third segment 164 is provided for the acquisition of gradients in an orientation "y", wherein y is essentially perpendicular to x. If the first segment 161 is placed above the line detector sensor, conventional scanning is performed, if the second segment 162 is placed above the line detector sensor, a gradient in x-direction is measured, and if the third segment 164 is placed above the line detector sensor, a gradient in y-direction is measured. It is further possible to employ at least a further segment (not shown) with a grating orientation of e.g. 45° in between the second and third segments 162, 164.

FIG. 4 shows a schematic overview of steps of an X-ray imaging method. The method comprises the following steps, not necessarily in this order:

In a first step S1, an X-ray beam 11 is provided with an X-ray source arrangement to an object to be imaged.

In a second step S2, an interference pattern is generated with at least one grating 13, 14 that comprises at least a first segment 161 and a second segment 162 arranged adjacent to each other in a direction perpendicular to the direction of a line detector 15.

In a third step S3, a line detector 15 with a plurality of sensor lines, which sensor lines are each provided by a plurality of sensor elements, and which sensor lines are provided for detecting the respective portions of the X-ray beam 11 passing the grating during operation and the object 21 to be imaged are moved relative to each other, such that in response to the portions of the X-ray beam a number of interference patterns are detected at respective different relative positions of the line detector and the object for reconstructing an image of the object 21.

In a fourth step S4, the line detector 15 and the grating are moved relative to each other between at least a first relative position and a second relative position, such that in the first relative position, a portion of the X-ray beam 11 during operation is passing through the at least one first segment 161, while the at least one second segment 162 is arranged outside said portion of the X-ray beam 11, and that in the second relative position, said portion of the X-ray beam 11 during operation is passing through the at least one second segment 162, while the at least one first segment 161 is arranged outside said portion of the X-ray beam 11.

In a fifth step S5, the portion of the X-ray beam 11 passing the grating is detected.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it, which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray imaging device, comprising:
    an X-ray source arrangement for providing an X-ray beam;
    at least one grating; and
    a line detector with a plurality of sensor lines, which sensor lines are each provided by a plurality of sensor elements, and which sensor lines are provided for detecting respective portions of the X-ray beam passing the at least one grating during operation;
    wherein the X-ray imaging device is arranged for moving the line detector and an object to be imaged relative to each other, such that in response to the portions of the X-ray beam a number of interference patterns are detectable at respective different relative positions of the line detector and the object for reconstructing an image of the object;
    wherein the at least one grating comprises at least one first segment and at least one second segment arranged adjacent to each other in a direction perpendicular to the direction of the line detector; and
    wherein the X-ray imaging device is arranged for moving the line detector and the at least one grating relative to each other between at least a first relative position and a second relative position, such that in the first relative position, a portion of the X-ray beam during operation passes through the at least one first segment, while the at least one second segment is arranged outside said portion of the X-ray beam, and that in the second relative position, said portion of the X-ray beam during operation passes through the at least one second segment, while the at least one first segment is arranged outside said portion of the X-ray beam.

2. The X-ray imaging device according to claim 1, wherein each of the first and the second segments comprises a grating structure of a respective transmission characteristic and wherein the first and the second segments differ in terms of the respective grating structure such that the first and the second segments differ in terms of the respective transmission characteristic.

3. The X-ray imaging device according to claim 2, wherein the grating structure of the first segment has a first grating pitch; and
    wherein the grating structure of the second segment has a second grating pitch that differs from the first grating pitch.

4. The X-ray imaging device according to claim 2, wherein the grating structure of the first segment has a first orientation; and
    wherein the grating structure of the second segment has a second orientation that differs from the first orientation.

5. The X-ray imaging device according to claim 2, wherein the grating structure of the first segment has a first geometry; and
    wherein the grating structure of the second segment has a second geometry that differs from the first geometry.

6. The X-ray imaging device according to claim 1, wherein the at least one grating comprises a frame; and
    wherein the frame comprises at least the first and second segments.

7. The X-ray imaging device according to claim 1, wherein the at least one grating comprises at least one third segment arranged adjacent to the second segment in a direction perpendicular to the direction of the line detector;
    wherein the at least one third segment differs from the first and the second segments in terms of the respective grating structure and the respective transmission characteristic; and
    wherein the X-ray imaging device is arranged for moving the line detector and the at least one grating relative to each also to a third relative position, such that in the third relative position, the portion of the X-ray beam during operation passes through the at least one third segment, while the first and second segments are arranged outside said portion of the X-ray beam, and that in the first and second relative position, the at least one third segment is arranged outside said portion of the X-ray beam.

8. The X-ray imaging device according to claim 1, wherein the X-ray imaging device is an X-ray differential phase contrast imaging device; and
    wherein the at least one grating is provided as a phase grating, or as an absorber grating.

9. The X-ray imaging device according to claim 1, wherein two of the at least one grating are provided;
    wherein one of the two gratings is a phase grating and the other one of the two gratings is an absorber grating installed relative to the phase grating downstream the X-ray beam; and
    wherein, preferably, the first segments of the phase grating are different than the first segments of the absorber grating; and/or the second segments of the phase grating are different than the second segments of the absorber grating.

10. The X-ray imaging device according to claim 1, further comprising a displacement unit configured for moving the at least one grating relative to the line detector.

11. The X-ray imaging device according to claim 1, wherein the at least one grating and the line detector are mounted to a movable gantry; and
    wherein, preferably, a gantry displacement unit is provided that is configured for moving the movable gantry relative to the object to be imaged.

12. An X-ray imaging system, comprising:
    an X-ray imaging device;
    a processing unit; and an object-receiving device configured to receive an object to be imaged;

wherein the X-ray imaging device comprises:

an X-ray source arrangement for providing an X-ray beam;

at least one grating; and a line detector with a plurality of sensor lines, which sensor lines are each provided by a plurality of sensor elements, and which sensor lines are provided for detecting respective portions of the X-ray beam passing the at least one grating during operation;

wherein the X-ray imaging device is arranged for moving the line detector and an object to be imaged relative to each other, such that in response to the portions of the X-ray beam a number of interference patterns are detectable at respective different relative positions of the line detector and the object for reconstructing an image of the object;

wherein the at least one grating comprises at least one first segment and at least one second segment arranged adjacent to each other in a direction perpendicular to the direction of the line detector; and wherein the X-ray imaging device is arranged for moving the line detector and the at least one grating relative to each other between at least a first relative position and a second relative position, such that in the first relative position, a portion of the X-ray beam during operation passes through the at least one first segment, while the at least one second segment is arranged outside said portion of the X-ray beam, and that in the second relative position, said portion of the X-ray beam during operation passes through the at least one second segment, while the at least one first segment is arranged outside said portion of the X-ray beam; and wherein the processing unit is configured to control a relative movement of the X-ray imaging device and the object-receiving device in relation to each other, and/or a relative movement of the at least one grating and the line detector of the X-ray imaging device in relation to each other.

13. An X-ray imaging method, comprising:

providing an X-ray beam with an X-ray source arrangement to an object to be imaged;

generating an interference pattern with at least one grating that comprises at least a first segment and a second segment arranged adjacent to each other in a direction perpendicular to the direction of a line detector;

relatively moving a line detector with a plurality of sensor lines, which sensor lines are each provided by a plurality of sensor elements, and which sensor lines are provided for detecting respective portions of the X-ray beam passing the at least one grating during operation and the object to be imaged, such that in response to the portions of the X-ray beam a number of interference patterns are detected at respective different relative positions of the line detector and the object for reconstructing an image of the object;

relatively moving the line detector and the at least one grating between at least a first relative position and a second relative position, such that in the first relative position, a portion of the X-ray beam during operation is passing through the at least one first segment, while the at least one second segment is arranged outside said portion of the X-ray beam, and that in the second relative position, said portion of the X-ray beam during operation is passing through the at least one second segment, while the at least one first segment is arranged outside the said portion of the X-ray beam; and detecting the portion of the X-ray beam passing the at least one grating.

14. A non-transitory computer readable medium storing a computer program element for controlling an X-ray imaging device or an X-ray imaging system, which, when being executed by a processing unit, is adapted to perform the method according to claim 13.

* * * * *